(12) United States Patent
Shyur et al.

(10) Patent No.: US 7,547,455 B2
(45) Date of Patent: Jun. 16, 2009

(54) CANCER AND INFLAMMATORY DISORDER TREATMENT

(75) Inventors: Lie-Fen Shyur, Taipei (TW); Chia-Chung Hou, Tainan (TW); Jyh-Horng Wu, Chiayi (TW); Yi-Ping Chen, Keelung (TW); Sheng-Yang Wang, Shin-Dian (TW); Chi-Chang Huang, Pinglin Township, Taipei County (TW); Ning-Sun Yang, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 11/858,629

(22) Filed: Sep. 20, 2007

(65) Prior Publication Data

US 2008/0152737 A1 Jun. 26, 2008

Related U.S. Application Data

(60) Provisional application No. 60/943,768, filed on Jun. 13, 2007, provisional application No. 60/845,760, filed on Sep. 20, 2006.

(51) Int. Cl.
*A61K 36/00* (2006.01)

(52) U.S. Cl. .................................................. 424/725

(58) Field of Classification Search ........................ None
See application file for complete search history.

(56) References Cited

U.S. PATENT DOCUMENTS 5,620,962 A 4/1997 Winget
5,767,095 A 6/1998 Winget
7,084,122 B2 8/2006 Larsen et al.
2003/0139350 A1 7/2003 Larsen et al.

OTHER PUBLICATIONS

Iwalewa et al. (J. Medicinal Food (Dec. 2005), vol. 8, No. 4, pp. 539-544).*
Bruno et al., "Selective in vivo Anti-Inflammatory Action of the Galactolipid Monogalactosyldiacylglycerol," European Journal of Pharmacology, 524:159-168 (2005).
Jayaprakasam et al., "Tumor Cell Proliferation and Cyclooxygenase Enzyme Inhibitory Compounds in *Amaranthus tricolor*," J. Agric. Food Chem., 52:6939-6943 (2004).
Larsen et al., "An Antiinflammatory Galactolipid from Rose Hip (*Rosa canina*) that Inhibits Chemotaxis of Human Peripheral Blood Neutrophils in Vitro," J. Nat. Prod., 66:994-995 (2003).
Maeda et al., "Inhibitory Effect on Replicative DNA Polymerases, Human Cancer Cell Proliferation, and In Vivo Anti-Tumor Activity by Glycolipids from Spinach," Current Medicinal Chemistry, 14:955-967 (2007).
Mizushima et al., "Galactosyldiacylglycerol, a Mammalian DNA Polymerase α-Specific Inhibitor from a Sea Alga, *Petalonia bingnamiae*," Biol. Pharm. Bull. 24(9):982-987 (2001).
Murakami et al., "Glyceroglycolipids from *Citrus hystrix*, a Traditional Heb in Thailand, Potently Inhibit the Tumor-Promoting Activity of 12-O-Tetradecanoylphorbol 13-Acetate in Mouse Skin," J. Agric. Food Chem., 43:2779-2783 (1995).

* cited by examiner

*Primary Examiner*—Susan C Hoffman
(74) *Attorney, Agent, or Firm*—Occhiuti Rohlicek & Tsao LLP

(57) ABSTRACT

Disclosed are extracts, compositions, and methods for treating cancer and inflammatory disorders. Also disclosed are methods for preparing extracts or compounds for treating the disorders.

14 Claims, 3 Drawing Sheets

A. RP-HPLC analysis of CREa8 fraction of *C. rabens*

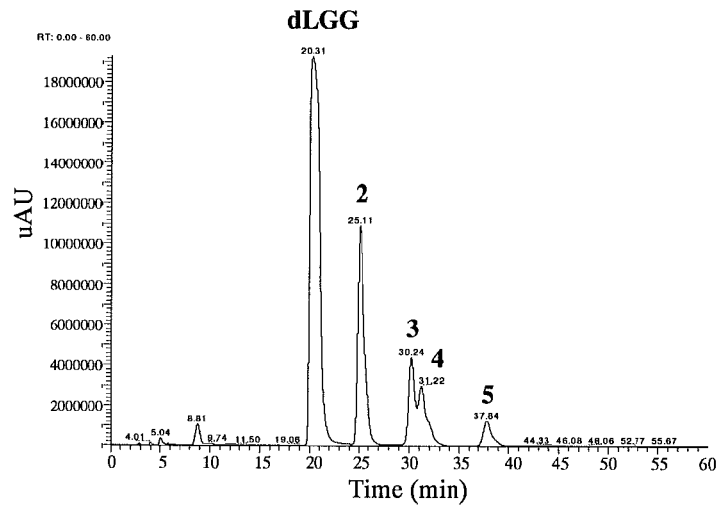

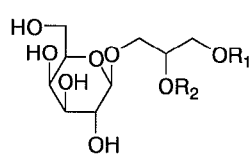

|  | $R_1$ (or $R_2$) | $R_2$ (or $R_1$) |
|---|---|---|
| dLGG | α-linolenic acid (18:3) | α-linolenic acid (18:3) |
| 2 | α-linoleic acid (18:2) | α-linolenic acid (18:3) |
| 3 | palmitic acid (16:0) | α-linolenic acid (18:3) |
| 4 | oleic acid (18:1) | α-linolenic acid (18:3) |
| 5 | palmitic acid (16:0) | α-linoleic acid (18:2) |

B. APCI-MS data of five major monogalactosyldiacylglycerols in CREa8 fraction

| ion | peak | | | | |
|---|---|---|---|---|---|
|  | dLGG | 2 | 3 | 4 | 5 |
| $m/z$ [M+Na]$^+$ | 797 (3) | 799 (4) | 775 (1) | 801 (5) | 777 (8) |
| diacylglycerol moiety | | | | | |
| [CH$_2$(OCOR$^1$)CH(OCOR$^2$)CH$_2$OH]$^+$ | 613 (100) | 615 (100) | 591 (54) | 617 (100) | 593 (25) |
| [CH$_2$(OCOR$^1$)CH(OCOR$^2$)CH$_2$]$^+$ | 595 (42) | 597 (51) | 573 (43) | 599 (57) | 575 (100) |
| monoacylglycerol moiety | | | | | |
| [CH$_2$(OCOR$^1$)CH(OH)CH$_2$]$^+$ and | 335 (95) | 337 (61) | 313 (96) | 339 (10) | 313 (79) |
| [CH$_2$(OH)CH(OCOR$^2$)CH$_2$]$^+$ |  | 335 (53) | 335 (100) | 335 (27) | 337 (47) |
| acyl moiety | | | | | |
| [R$^1$]$^+$ and [R$^2$]$^+$ | 261 (33) | 263 (16) | 239 (1) | 265 (3) | 239 (11) |
|  |  | 261 (31) | 261 (45) | 261 (17) | 263 (20) |
| retention time (min) | 20.31 | 25.11 | 30.24 | 31.22 | 37.84 |
| molecular species (fatty acid/fatty acid)[a] | 18:3/18:3 | 18:2/18:3 | 16:0/18:3 | 18:1/18:3 | 16:0/18:2 |
| % (peak percentage)[b] | 65.7 | 20.5 | 6.5 | 4.7 | 2.5 |

[a] Abbreviations: 18:3, α-linolenic acid; 18:2, α-linoleic acid; 18:1, oleic acid; 16:0, palmitic acid. The *sn* positions of fatty acids are not determinated.
[b] Values indicate the peak percentage of total monogalactosyldiacylglycerol peak area

FIGs. 3A and 3B

CANCER AND INFLAMMATORY DISORDER TREATMENT

RELATED APPLICATION

This application claims priority to U.S. provisional application Ser. No. 60/845,760 filed on Sep. 20, 2006; and U.S. provisional application Ser. No. 60/943,768, filed on Jun. 13, 2007, the contents of which are incorporated by reference in their entirety.

BACKGROUND

Cancer is the second leading cause of death in the United States, exceeded only by heart disease. It features an abnormal mass of malignant tissue resulting from excessive cell division. Cancer cells proliferate in defiance of normal restraints on cell growth, and invade and colonize territories normally reserved for other cells. Modes of cancer therapy include chemotherapy, surgery, radiation, and combinations of these treatments. Chemotherapy typically involves use of one or more compounds that inhibit cancer cell growth. While many cancer chemotherapeutic agents have been developed, there remains a need for more effective chemotherapy. Inflammation is the body's defense reaction to injuries such as those caused by mechanical damage, infection, or antigenic stimulation. An inflammatory reaction may be expressed pathologically when inflammation is induced by an inappropriate stimulus such as an autoantigen, expressed in an exaggerated manner or persists well after the removal of the injurious agents. A number of therapeutic agents have been developed for inhibiting inflammatory reactions or treating inflammatory disorders. However, many of them are not satisfactory due to poor efficacy, side effects, or instability.

There is a need for agents and methods for treating cellular proliferative disorders, such as cancer, or for treating inflammatory disorders

SUMMARY

This invention relates to an extract prepared from *Crassocephalum* plants and its use in treating cellular proliferative disorders or treating inflammatory disorders.

One aspect of the invention features an extract prepared from *Crassocephalum. rabens*, also known as *C. rabens* S. Moore, *C. rabens* S. Moore, and *C. crepidioides* S. Moore. The extract is prepared by a process including mixing a *C. rabens* plant with alcohol to form a first solution; removing alcohol from the first solution to obtain a second solution; adding ethyl acetate to the second solution to form an organic portion and an inorganic portion (or, water portion); separating the organic portion into a multiple fractions; and collecting a fraction containing a galactolipid compound. The galactolipid compound can be 1,2-di-O-α-linolenoyl-3-O-β-galactopyranosyl-sn-glycerol (dLGG) or 1(2)-O-α-linolenoyl-2(1)-O-α-linoleoyl 3-O-β-galactopyranosyl-sn-glycerol (18:3/18:2) (dLLGG). These two compounds can be at a weight ratio of 1:0.1 to 1:0.3.

The organic portion can be separated on a silica gel column with a solution containing dichloromethane and methanol (ratio: 80-90%:10-20%) to obtain the fraction containing a galactolipid compound. The extract can include a monogalactosyldiacylglycerol of formula I:

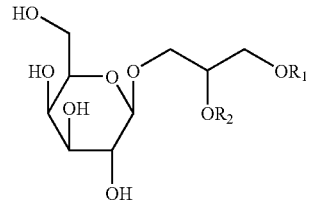

wherein of $R_1$ and $R_2$, independently, is $C(O)R_a$ in which $R_a$ is $C_{15-17}$ alkyl having 0 to 3 double bonds. In one embodiment, the monogalactosyldiacylglycerol is selected from the group consisting of 1,2-di-O-α-linolenoyl-3-O-β-galactopyranosyl-sn-glycerol (dLGG), 1(2)-O-α-linolenoyl-2(1)-O-α-linoleoyl 3-O-β-galactopyranosyl-sn-glycerol (18:3/18:2) (dLLGG), 1(2)-O-α-linolenoyl-2(1)-O-α-palmitoyl 3-O-β-galactopyranosyl-sn-glycerol (18:3/16:0), 1(2)-O-α-linolenoyl-2(1)-O-α-oleoyl 3-O-β-galactopyranosyl-sn-glycerol (18:3/18:1), and 1(2)-O-α-linoleoyl-2(1)-O-α-palmitoyl 3-O-β-galactopyranosyl-sn-glycerol (18:2/16:0). The ratio of these five compounds in sequence can be: 1:0.1-0.3:0.001-0.1:0.001-0.07:0.001-0.04. The extract can inhibit NO production of a cell or the expression of iNOS or COX-2 in a cell. It can also inhibit the activity of NF-κB in a cell.

Within the scope of this invention is a composition containing the above-described extract and a carrier, such as a cosmetically acceptable carrier or a pharmaceutically acceptable carrier. The composition can further include 1,2-di-O-α-linolenoyl-sn-glycerol (dLG), 2-O-α-linolenoyl-3-O-β-galactopyranosyl-sn-glycerol (2LGG), or 1-O-α-linolenoyl-3-O-β-galactopyranosyl-sn-glycerol (1LGG).

Another aspect of the invention features a method of making the above-described extract. The method includes mixing a *C. rabens* plant with alcohol to form a first solution; removing alcohol from the first solution to obtain a second solution; adding ethyl acetate to the second solution to form an organic portion and a water portion; separating the organic portion into a multiple fractions; and collecting a fraction containing a galactolipid compound.

In another aspect, the invention features a method of treating an inflammatory disorder, e.g., a skin disorder, in a subject. The method includes administering to a subject in need thereof an effective amount of the extract or composition described above. A "subject" refers to a human and a non-human animal. Examples of a non-human animal include all vertebrates, e.g., mammals, such as non-human primates (particularly higher primates), dog, rodent (e.g., mouse or rat), guinea pig, cat, and non-mammals, such as birds, amphibians, reptiles, etc. In a preferred embodiment, the subject is a human. In another embodiment, the subject is an experimental animal or animal suitable as a disease model.

The invention also features a method of treating a cellular proliferative disorder in a subject. The method includes administering to a subject in need thereof an effective amount of the extract or composition described above. Examples of the disorder include a cancer, such as a skin tumor.

The invention further features a method for inhibiting the expression of iNOS or COX-2 in a cell, or a method for inhibiting the expression or activity of NF-κB in a cell. The method includes contacting a cell with the extract or composition described above.

The details of one or more embodiments of the invention are set forth in the accompanying description below. Other features, objects, and advantages of the invention will be apparent from the detailed description, drawings, and the claims.

BRIEF DESCRIPTION OF DRAWINGS

FIGS. 3A and 3B are a graph and tables showing results of HPLC-APCI/MS analysis of metabolite profiling of CREa8 and structural elucidation of dLGG.

DETAILED DESCRIPTION

Figure 1:
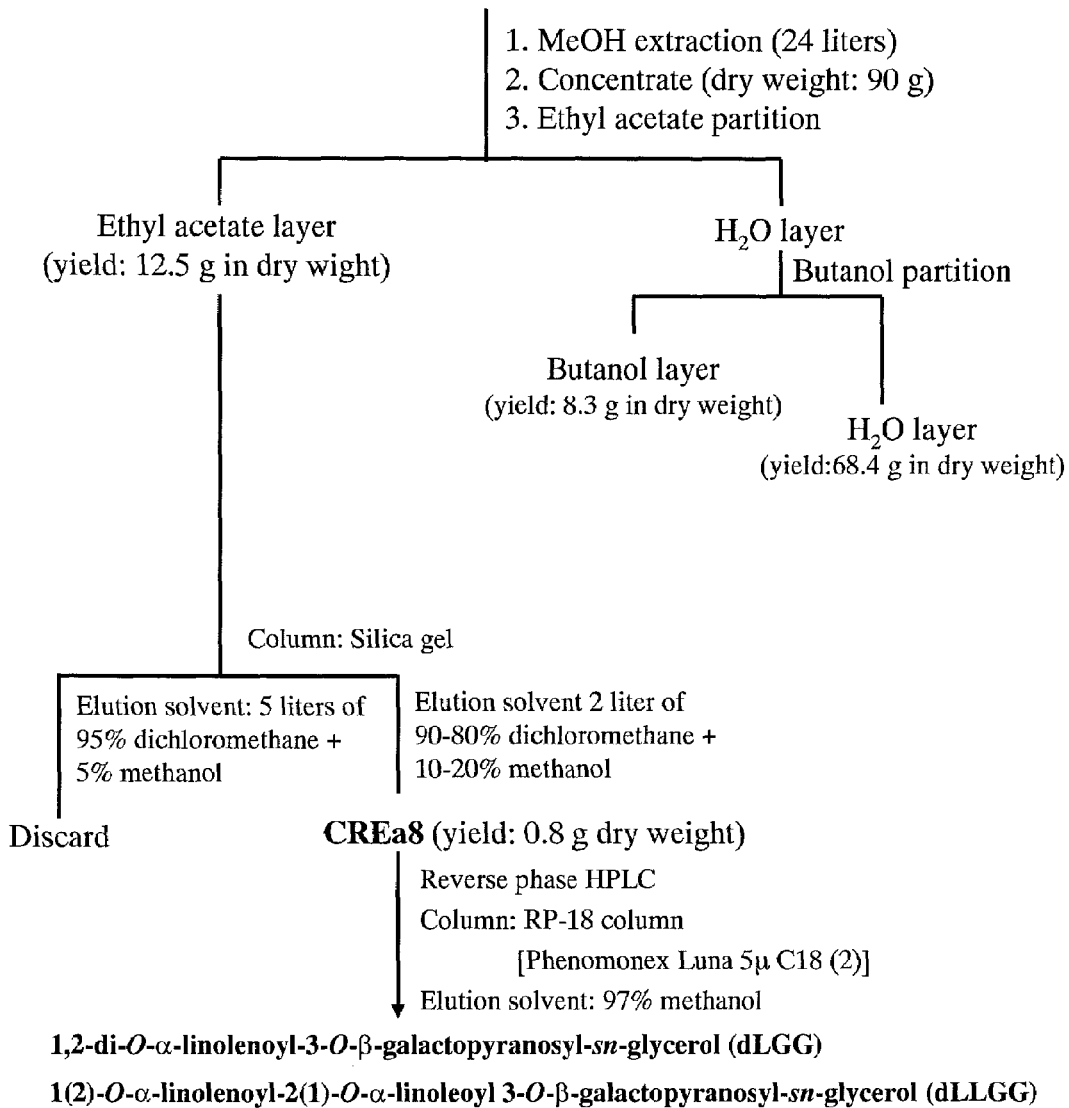
FIG. 1 is a diagram showing an exemplary scheme for preparing and characterizing total plant extracts, subfractions, and phytocompounds from *C. rabens*.

This invention is based, at least in part, on the unexpected finding that extracts and compounds prepared from *Crassocephalum rabens* are effective in inhibiting key enzymes and key transcription factor that are involved in inflammation and tumorigenesis, such as inducible nitric oxide synthase (iNOS), Cycloxygenase-2 (COX-2), and NF-κB.

It was known that iNOS is involved in the production of nitric oxide (NO). NO and its metabolite, peroxynitrite, are mutagenic because they deaminate DNA and inactivate DNA repair enzymes. NO is produced by the oxidative deamination of L-arginine at inflammatory sites by iNOS, which is expressed in response to a variety of pro-inflammatory cytokines and bacterial lipopolysaccharide (LPS). Improper expression of iNOS has been found to be associated with the pathophysiology of certain human cancers and inflammatory disorders. COX-2 is another important enzyme in the pathophysiology of inflammation and carcinogenesis through its synthesis of the precursors of prostaglandins and thromboxanes. COX-2 is expressed within human tumor neovasculature as well as in neoplastic cells in human prostate, colon, breast, and lung cancer tissues. Since inflammation is closely linked to tumor promotion, substances with potent anti-inflammatory activities are also anticipated to have chemopreventive effects on carcinogenesis, especially selective inhibitors of both COX-2 and iNOS.

NF-κB, one of the principal inducible transcription factors in mammals, plays a pivotal role in inflammation through regulation of COX-2 and iNOS expression. NF-κB signaling involves an integrated sequence of protein-regulated steps, many of which are potential targets for inflammation and cancer treatments. NF-κB is maintained as an inactive cytoplasmic form through its association with an inhibitory molecule IκB. Exposure of cells to a variety of external stimuli including cytokines, radiation, LPS, and reactive oxygen species causes rapid phosphorylation of IκB, with subsequent dissociation and proteosomic degradation, allowing activated free NF-κB dimers to translocate to the nucleus and induce transcription of many target genes.

Within the scope of this invention is an extract (such as CREa8, which contains dLGG, as described below) from *C. rabens*. The extract exhibits significant activity of inhibiting NO production and the iNOS and COX-2 expression.

The extract can be prepared by mixing a *C. rabens* plant with a solvent, such as methanol or ethanol, in room temperature for 1 to 3 days. The resulting plant extracts can be further separated to generate extract subfractions using organic solvents, such as ethyl acetate (EA). The fraction containing a galactolipid compound is collected to generate the extract. The extract can be further fractionated on silica and RP-18 gel using organic solvents to obtain an enriched, bioactive subfraction (such as CREa8 described below). The active constituents can be further isolated and identified from the bioactive CREa8 fraction by chromatography techniques, such as HPLC. The active constituents include galactolipids, e.g., dLGG, which can be isolated from the plant extracts of *C. rabens* or other plant species that contain these compounds or their derivatives. The fractions can contain marker substrate (dLGG) and other galactolipid compounds.

The bioactivities of inhibiting NO production or iNOS and COX-2 expression can be tested using a number of bioassays described below, such as a NO production inhibitory assay and a COX-2 reporter/luciferase assay. The confirmed extract or fraction can be further processed to obtain active compounds. As described in the examples below, the metabolite profiling of active fraction CREa8 can be analyzed by HPLC and HPLC-APCIMS. The metabolite profiling can be applied on the QA/QC of the active fraction (e.g., CREa8) of *C. rabens*. dLGG can be used as the marker substance on QA/QC of the active fraction of *C. rabens*. The C. rabens bioactive fraction can contain the marker substance (dLGG) in a range from 15 to 90% (e.g., 15-60%) of the weight of a preparation.

As described in the example section below, it was found that the above-described extract, fraction, or compound can suppress NF-κB and its downstream inflammatory mediators, NO, iNOS, COX-2 and $PGE_2$ in vitro, and inhibit growth of cancer cells, e.g., B16 melanoma. For example, the bioactive glyceroglycolipid, 1,2-di-O-α-linolenoyl-3-O-β-galactopyranosyl-sn-glycerol (dLGG) was found to be a potent NO scavenger in vitro and in vivo. dLGG treatment inhibited both mRNA and protein expression of iNOS and COX-2 in murine macrophages, and inhibited COX-2 gene transcription in 12-O-tetradecanoylphorbol-13-acetate (TPA)-treated B16 cells. In immunohistochemical studies, dLGG inhibited TPA-induced expression of COX-2 and nitration of proteins in mouse skin. dLGG could also significantly inhibit LPS-induced $PGE_2$ production in murine macrophages. Furthermore, dLGG prevented nuclear translocation of cytoplasmic NF-κB by suppressing IκBα phosphorylation and degradation. Structure-activity relationship study by electrophoretic mobility shift assay indicated that the dilinolenoylglycerol moiety in dLGG is the essential structural feature preventing NF-κB-DNA complex formation. A dLGG-enriched extract from *C. rabens* (10 mg/kg) markedly suppressed B16 melanoma growth in C57BL/6J mice following intraperitoneal administration, an effect comparable to that of cisplatin, a cancer chemotherapeutic drug. Thus, the above-described extract, fraction, or compound can be used to control tumor growth or treat inflammatory disorders.

Accordingly, within the scope of this invention is a composition that contains a suitable carrier and one or more of the extract or compounds described above. The composition can be a pharmaceutical composition that contains a pharmaceutically acceptable carrier or a cosmetic composition that contains a cosmetically acceptable suitable carrier. Preferably, a compound is added to the composition in pure form. A pure compound refers to a compound substantially free from naturally associated molecules, i.e., at least 75% pure by dry weight. Purity can be measured by any appropriate standard method, for example, by HPLC analysis. The compounds described above can be chemically synthesized or purified from herbs. For example, it can be isolated from plants of the *Crassocephalum rabens* family.

Examples of a composition of the present invention include, but are not limited to, foods, food additives, nutritional supplements, and pharmaceutical preparations. It may be in the form of tablets, suspensions, implants, solutions, emulsions, capsules, powders, syrups, liquid compositions, ointments, lotions, creams, pastes, gels, or the like.

As a dietary supplement, additional nutrients, such as minerals or amino acids, may be included. A dietary composition can also be a drink or food product. As used herein, the terms "drink" and "food" broadly refer to any kinds of liquid and solid/semi-solid materials, respectively, that are used for nourishing an animal, and for sustaining normal or accelerated growth of an animal including a human. Examples of the drink product include, but are not limited to, tea-based beverages, juice, coffee, and milk. Examples of the food product include jelly, cookies, cereals, chocolates, snack bars, chewing gum, herbal extracts, dairy products (e.g., ice cream, and yogurt), soy bean product (e.g., tofu), and rice products.

A composition of the present invention may include a carrier. Depending on the kind of the composition, a carrier may be a suitable dietary carrier or a pharmaceutically acceptable carrier. Examples of a pharmaceutically acceptable carrier include, but are not limited to, biocompatible vehicles, adjuvants, additives, and diluents to achieve a composition usable as a dosage form.

A "pharmaceutically acceptable carrier," after administered to or upon a subject, does not cause undesirable physiological effects. The carrier in the pharmaceutical composition must be "acceptable" also in the sense that it is compatible with the active ingredient and, preferably, capable of stabilizing it. One or more solubilizing agents can be utilized as pharmaceutical carriers for delivery of an active compound. Examples of other carriers include colloidal silicon oxide, magnesium stearate, cellulose, sodium lauryl sulfate, and D&C Yellow #10.

The above-described composition, in any of the forms described above, can be used for treating inflammation-related disorders or cellular proliferation disorders. The term "treating" refers to the administration of an effective amount of a composition of the invention to a subject who has one of the above-described diseases or conditions, a symptom of such a disease, or a predisposition toward such a disease or condition, with the purpose to confer a therapeutic effect, e.g., to cure, relieve, alter, affect, ameliorate, or prevent the disease or condition, the symptom of it, or the predisposition toward it. An "effective amount" refers to the amount of an active compound that is required to confer a therapeutic effect on a treated subject. Effective doses will vary, as recognized by those skilled in the art, depending on the types of diseases treated, route of administration, excipient usage, and the possibility of co-usage with other therapeutic treatment.

An inflammation-related disorder is characterized by a local or systemic, acute or chronic inflammation. Examples include inflammatory dermatoses (e.g., dermatitis, eczema, atopic dermatitis, allergic contact dermatitis, urticaria, necrotizing vasculitis, cutaneous vasculitis, hypersensitivity vasculitis, eosinophilic myositis, polymyositis, dermatomyositis, and eosinophilic fasciitis), inflammatory bowel diseases (e.g., Crohn's disease and ulcerative colitis), hypersensitivity lung diseases (e.g., hypersensitivity pneumonitis, eosinophilic pneumonia, delayed-type hypersensitivity, interstitial lung disease or ILD, idiopathic pulmonary fibrosis, and ILD associated with rheumatoid arthritis), asthma, and allergic rhinitis. Examples also include autoimmune diseases (e.g., rheumatoid arthritis, psoriatic arthritis, systemic lupus erythematosus, myasthenia gravis, juvenile onset diabetes, glomerulonephritis, autoimmune throiditis, ankylosing spondylitis, systemic sclerosis, and multiple sclerosis), acute and chronic inflammatory diseases (e.g., systemic anaphylaxia or hypersensitivity responses, drug allergies, insect sting allergies, allograft rejection, and graft-versus-host disease), Sjogren's syndrome, human immunodeficiency virus infection, cancer (e.g., brain, breast, prostate, colon, kidney, ovary, thyroid, lung, and haematopoietic cancer), and tumor metastasis.

A cellular proliferative disorder refers to a disorder characterized by uncontrolled, autonomous cell growth, including malignant and non-malignant growth. Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the terms "cancer", "hyperproliferative" and "neoplastic" refer to cells having the capacity for autonomous growth. Examples of such cells include cells having an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

Additional examples of proliferative disorders include hematopoietic neoplastic disorders. As used herein, the term "hematopoietic neoplastic disorders" includes diseases involving hyperplastic/neoplastic cells of hematopoietic origin. A hematopoietic neoplastic disorder can arise from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia, Hodgkin's disease and Reed-Sternberg disease.

The compounds, extract, and methods described herein can also be used to treat COX-2- or NOS-related disorders, that is, disorders associated with abnormal expression of COX-2 or NOS.

A pharmaceutical composition of this invention can be administered parenterally, orally, nasally, rectally, topically, intratumorally, or buccally. The term "parenteral" as used herein refers to subcutaneous, intracutaneous, intravenous, intrmuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition having an active compound can also be administered in the form of suppositories for rectal administration.

A topical composition contains a safe and effective amount of a dermatologically acceptable carrier suitable for application to the skin. Generally, a topical composition can be solid, semi-solid, cream, or liquid. It may be a cosmetic or dermatologic product in the form of an ointment, lotion, foam, cream, gel, or solution. Details about dermatologically acceptable carriers are provided below.

The compounds and extracts described above can be preliminarily screened for their efficacy in treating above-described diseases by an in vitro assay (See Examples below) and then confirmed by animal experiments and clinic trials. Other methods will also be apparent to those of ordinary skill in the art.

A composition of the present invention may be used alone or in combination with other biologically active ingredients. Alone or in combination with other active ingredients, it may be administered to a subject in a single dose or multiple doses over a period of time. Various administration patterns will be apparent to those skilled in the art. The dosage ranges for the administration of the composition are those large enough to produce the desired effect. The dosage should not be so large as to cause any adverse side effects, such as unwanted cross-reactions and the like. Generally, the dosage will vary with the age, weight, sex, condition, and extent of a condition in a subject, and the intended purpose. The dosage can be determined by one of skill in the art without undue experimentation. The dosage can be adjusted in the event of any counter indications, tolerance, or similar conditions. Those of skill in the art can readily evaluate such factors and, based on this information, determine the particular effective concentration of a composition of the present invention to be used for an intended purpose.

Also within the scope of this invention is a cosmetic composition. This composition contains a safe and effective amount of a dermatologically acceptable carrier that is suitable for topical application to the skin. It enables an active compound or extract and optional component to be delivered to the skin at an appropriate concentration(s). The carrier can thus act as a diluent, dispersant, solvent, or the like to ensure that the active materials are applied to and distributed evenly over the selected target at an appropriate concentration. The carrier can be solid, semi-solid, or liquid. Preferably, it is in the form of a lotion, a cream, or a gel, in particular one that has a sufficient thickness or yield point to prevent the active materials from sedimenting. The carrier can be inert or possess dermatological benefits of its own. It should also be physically and chemically compatible with the active components described herein, and should not unduly impair stability, efficacy, or other use benefits associated with the composition.

The type of carrier utilized in the cosmetic composition depends on the type of product form of the composition. A cosmetic composition may be made into a wide variety of product forms such as those known in the art. These include, but are not limited to, lotions, creams, gels, sticks, sprays, ointments, pastes, and mousses. These product forms may comprise several types of carriers including, but not limited to, solutions, aerosols, emulsions, gels, solids, and liposomes.

Preferred carriers can contain a dermatologically acceptable, hydrophilic diluent. Suitable hydrophilic diluents include water, organic hydrophilic diluents, such as $C_1$-$C_4$ monohydric alcohols and low molecular weight glycols and polyols (including propylene glycol, polyethylene glycol of, e.g., MW 200-600), polypropylene glycol of, e.g., MW 425-2025, glycerol, butylene glycol, 1,2,4-butanetriol, sorbitol esters, 1,2,6-hexanetriol, ethanol, iso-propanol, sorbitol esters, ethoxylated ethers, propoxylated ethers, and combinations thereof. The composition preferably comprises at least about 60% of the hydrophilic diluent.

Preferred carriers also contain an emulsion having a hydrophilic phase, especially an aqueous phase, and a hydrophobic phase, e.g., a lipid, oil, or oily material. As well known to one skilled in the art, the hydrophilic phase will be dispersed in the hydrophobic phase, or vice versa, to form respectively hydrophilic or hydrophobic dispersed and continuous phases, depending on the composition ingredients. The term "dispersed phase," a term well-known to one skilled in the art, refers to a phase that exists as small particles or droplets suspended in and surrounded by a continuous phase. The dispersed phase is also known as the internal or discontinuous phase. The emulsion may be or contain (e.g., in a triple or other multi-phase emulsion) an oil-in-water emulsion or a water-in-oil emulsion such as a water-in-silicone emulsion. Oil-in-water emulsions typically comprise from 1% to 50% (preferably 1% to 30%) of the dispersed hydrophobic phase and from 1% to 99% (preferably from 40% to 90%) of the continuous hydrophilic phase; water-in-oil emulsions typically comprise from 1% to 98% (preferably from 40% to 90%) of the dispersed hydrophilic phase and from 1% to 50% (preferably 1% to 30%) of the continuous hydrophobic phase. The emulsion may also comprise a gel network, such as that described in G. M. Eccleston, Application of Emulsion Stability Theories to Mobile and Semisolid O/W Emulsions, Cosmetics & Toiletries, Vol. 101, November 1996, pp. 73-92, incorporated herein by reference. Preferred compositions herein are oil-in-water emulsions.

Preferred examples of a cosmetic composition of this invention have an apparent viscosity of from about 5,000 to about 200,000 mPa·s (centipoise). For example, preferred lotions have an apparent viscosity of from about 10,000 to about 40,000 mPa·s; and preferred creams have an apparent viscosity of from about 30,000 to about 160,000 mPa·s. Apparent viscosity can be determined using a Brookfield DVII RV viscometer, spindle TD, at 5 rpm, or the equivalent thereof. The viscosity is determined on a composition after the composition has been allowed to stabilize following its preparation, generally at least 24 hours under conditions of 25° C.±1° C. and ambient pressure after preparation of the composition. Apparent viscosity is measured with the composition at a temperature of 25° C.±1° C., after 30 seconds spindle rotation.

The cosmetic composition of the present invention is usually formulated to have a pH of 9.5 or below and in general have a pH in the range from 4.5 to 9, more preferably from 5 to 8.5. Some examples, particularly those containing an additional active agent such as salicylic acid, require a lower pH in order for the additional active to be fully efficacious. These compositions are usually formulated to have a pH of from 2.5 to 5, more preferably from 2.7 to 4.

The cosmetic composition may contain a wide variety of optional components, provided that such optional components are physically and chemically compatible with the essential components described herein, and do not unduly impair stability, efficacy, or other use benefits associated with the compositions. Optional components may be dispersed, dissolved, or the like in the carrier of the present compositions.

Exemplary optional components include emollients, oil absorbents, antimicrobial agents, binders, buffering agents, denaturants, cosmetic astringents, external analgesics, film formers, humectants, opacifying agents, perfumes, pigments, skin soothing and healing agents, preservatives, propellants, skin penetration enhancers, solvents, suspending agents, emulsifiers, cleansing agents, thickening agents, solubilising agents, waxes, sunscreens, sunless tanning agents, antioxidants and/or radical scavengers, chelating agents, anti-acne agents, anti-inflammatory agents, desquamation agents/exfoliants, organic hydroxy acids, vitamins, and natural extracts. Examples of such materials are described in Harry's Cosmeticology, 7th Ed., Harry & Wilkinson (Hill Publishers, London 1982); in Pharmaceutical Dosage Forms—Disperse Systems; Lieberman, Rieger & Banker, Vols. 1 (1988) & 2 (1989); Marcel Decker,. Inc.; in The Chemistry and Manufacture of Cosmetics, 2nd. Ed., deNavarre (Van Nostrand 1962-1965); and in The Handbook of Cosmetic Science and Technology, 1st Ed. Knowlton & Pearce (Elsevier 1993) can also be used in the present invention.

The cosmetic composition of the present invention is generally prepared by conventional methods known in the art of making topical compositions. Such methods typically involve mixing of the ingredients in one or more steps to a relatively uniform state, with or without heating, cooling, application of vacuum, and the like.

The cosmetic composition is useful for regulating or improving skin condition, including regulating visible or tactile wrinkles or discontinuities in skin, e.g., visible or tactile wrinkles or discontinuities in skin texture or color, more especially those associated with skin inflammation, ageing, or other internal factors (e.g., biochemical changes from within the skin) or external factors (e.g., ultraviolet radiation, environmental pollution, wind, heat, low humidity, harsh surfactants, and abrasives).

Regulating skin conditions can be carried out prophylactically or therapeutically. Prophylactical regulation includes delaying, minimizing, or preventing visible or tactile wrinkles or discontinuities in skin. Therapeutic regulation, on the other hand, includes ameliorating, diminishing, minimizing or effacing such wrinkles or discontinuities. Regulating skin conditions involves improving skin appearance feel, e.g., providing a smoother, more even appearance or feel and reducing signs of aging.

A cosmetic composition is topically applied to the skin in a safe and effective amount. The applied amount, the frequency of application, and the period of use vary widely depending upon the active levels of a given composition and the level of regulation desired. Typically, the composition can be applied once per day. However application rates can vary from about once per week up to about three times per day or more.

The cosmetic composition of this invention provides visible improvement in skin condition essentially immediately following application of the composition to the skin. Such immediate improvement involves covering or masking skin imperfections such as textural discontinuities (including those associated with skin inflammation or aging, e.g., enlarged pores), or providing a more even skin tone or color. The composition also provides visible improvement in skin condition following chronic topical application, e.g., one week, one year, or the subject's life time.

Regulating skin conditions is preferably performed by applying a composition in the form of a skin lotion, cream, cosmetic, or the like which is intended to be left on the skin for an extended period for some aesthetic, prophylactic, therapeutic or other benefits, i.e., a leave-on composition. After applying the composition to the skin, the leave-on composition is preferably left on the skin for a period of at least 15 minutes and up to 12 hours.

The specific example below is to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

EXAMPLE

Materials and Methods

Cell Lines and Culture Conditions

RAW 264.7 and B16 cells were obtained from the American Type Culture Collection (ATCC, MD). Macrophages were grown in Dulbecco's modified Eagle medium (DMEM) (Gibco/BRL, Grand Island, N.Y.), and B16 cells were grown at 37° C. in RPMI 1640 medium (Gibco/BRL), both supplemented with 10% heat-inactivated fetal bovine serum, 100 units/mL penicillin, and 100 μg/mL streptomycin, in a humidified 5% $CO_2$ incubator.

3-(4,5-Dimethylthiazol-2-yl)-2,5-diphenyltetrazolium bromide (MTT), 12-O-tetradecanoylphorbol-13-acetate (TPA), lipopolysaccharide (LPS), DTF, sodium nitroferricyanide (SNP), and 2-phenyl-4,4,5,5-tetramethylimidazoline-1-oxyl-3-oxide (PTIO) were purchased from Sigma Chemical Co. (St. Louis, Mo.). Celecoxib (CELEBREX™) was from Pharmacia (Northumberland, UK). Silica gel (230-400 mesh) and silica gel 60 $F_{254}$ TLC and RP-18 $F_{254s}$ TLC plates were purchased from Merck (Darmstadt, Germany). RP-18 silica gel (75$C_{18}$-OPN) was purchased from Cosmosil (Kyoto, Japan). All other chemicals and solvents were of reagent or HPLC grade.

Animals

Female C57BL/6J mice and female ICR mice (National Laboratory Animal Center, Taipei, Taiwan) were given a standard laboratory diet and distilled water ad libitum, and kept on a 12 hourslight/dark cycle at 22±2° C.

Isolation and Structure Elucidation of dLGG

Approximately 5.0 kg of fresh whole *C. rabens* (voucher specimen CB001 in Agricultural Biotechnology Research Center, Academia Sinica, Taiwan) was extracted with methanol (MeOH) at room temperature. Total MeOH extract was partitioned with ethyl acetate (EA) to yield the EA fraction (12.5 g) which was separated on a silica gel column with $CH_2Cl_2$-MeOH to yield subfractions 1-8. Subfraction 8 was further purified on a RP-18 silica gel column eluted with 95% MeOH to give a monogalactosyldiacylglycerol-enriched fraction (designated CREa8, 0.8 g). This subfraction, the most potent inhibitor of NO production in LPS-activated macrophages among the tested fractions, was further fractionated using semi-preparative RP-HPLC (Phenomonex Luna 5μ$C_{18}$ column, 250×10 $mm^2$). The metabolite profile of CREa8 was characterized and the content of dLGG was determined using RP-18 HPLC. Pure dLGG (~65.7% of dry weight of CREa8) had a retention time of 12 min (100% MeOH, 3.0 mL/min, $A_{205\,nm}$). $^1$H and $^{13}$C NMR spectra were recorded on a Brüker ADVANCE 500 AV spectrometer (Rheinstetten, Germany).

1,2-di-O-α-linolenoyl-3-O-β-galactopyranosyl-sn-glycerol (dLGG)

The characteristics of dLGG (colorless oil; ESI-MS m/z 797 [M+Na]$^+$; $^1$H and $^{13}$C NMR data (pyridine-$d_5$)) were consistent with previously published data (Murakami et al. J Agric Food Chem 1995; 43:2779-83). Atmospheric pressure chemical ionization/mass spectrometry (APCI/MS) was performed using a ThermoFinnigan/LCQ Advantage mass spectrometer, running in positive ion mode.

Preparation of Structural Analogs of dLGG dLGG in $H_2O$ was incubated with β-galactosidase (Sigma) at 37° C. for 2 days, and the product was extracted with ethyl acetate. The extract was evaporated to give 1,2-di-O-α-linolenoyl-sn-glycerol (dLG). dLG: colorless oil; ESI-MS m/z 635 [M+Na]$^+$; The structure of dLG was confirmed using 1D and 2D NMR spectroscopy.

dLGG (5 mg) was incubated with *Rhizopus arrhizus* lipase (1800 unit/5 mL in boric acid-borax buffer, pH 7.7) (Sigma) at 37° C. for 30 minutes. The reaction was stopped by adding 0.1 mL acetic acid and 3 mL ethanol. The solvent was evaporated and the residue separated by semi-preparative RP-18 HPLC with 90% MeOH to obtain 2-O-α-linolenoyl-3-O-β-galactopyranosyl-sn-glycerol (1.2 mg, 2LGG) and 1-O-α-linolenoyl-3-O-β-galactopyranosyl-sn-glycerol (0.8 mg, 1LGG). 2LGG and 1LGG: colorless oil; ESI-MS m/z 537 [M+Na]$^+$; $^1$H and $^{13}$C NMR data (pyridine-$d_5$) were consistent with previously published data (Murakami et al. J Agric Food Chem 1995; 43:2779-83.). Linolenic acid (LA) and stearic acid (SA) were from Sigma.

Measurement of NO Production and Cell Viability

RAW 264.7 cells were treated with compound for 1 hour, and then incubated for 24 hours with or without LPS. Nitrite levels in cell culture medium were determined using the Griess reaction (Chiang et al. Br J Pharmacol 2005; 146:352-63; Schmidt et al. Determination of nitrite and nitrate by the Griess reaction. In: Feelisch M, Stamler J S, editors. Methods In Nitric Oxide Research. New York: John Wiley & Sons Inc.; 1996. p. 491-7). Cell viability was examined using the MTT based assay (Scudiero et al. Cancer Res 1988; 48:4827-33).

Determination of Nitrite Concentration in Plasma

Female ICR mice were topically treated on their shaven back area of a 2-cm diameter (3.14 $cm^2$/site/mouse) with vehicle control (acetone), SNP (positive control), or with dLGG or PTIO for 30 minutes before SNP application. Mouse plasma samples were subjected to determine the nitrite content followed a published method (Moshage et al. Clin Chem 1995; 41:892-6.).

Cyclooxygenase-2 Activity Assays

COX-2 inhibition was measured with the chemiluminescent COX inhibitor screening assay kit (Cayman Chemical, Ann Arbor, Mich.).

Measurement of $PGE_2$ Production $PGE_2$ production was determined according to the procedure described in Chiang et al. Br J Pharmacol 2005; 146: 352-63. Macrophages were pretreated with aspirin (500 μM, 3 h) to inactivate endogenous cyclooxygenase-1, washed, and incubated with test compounds for 1 hour before further incubation for 16 hours with or without LPS. $PGE_2$ in the culture media was determined with ACE™ Competitive Enzyme Immunoassay (Cayman Chemical).

Reporter Gene Constructs and Luciferase Assays

Figure 2:
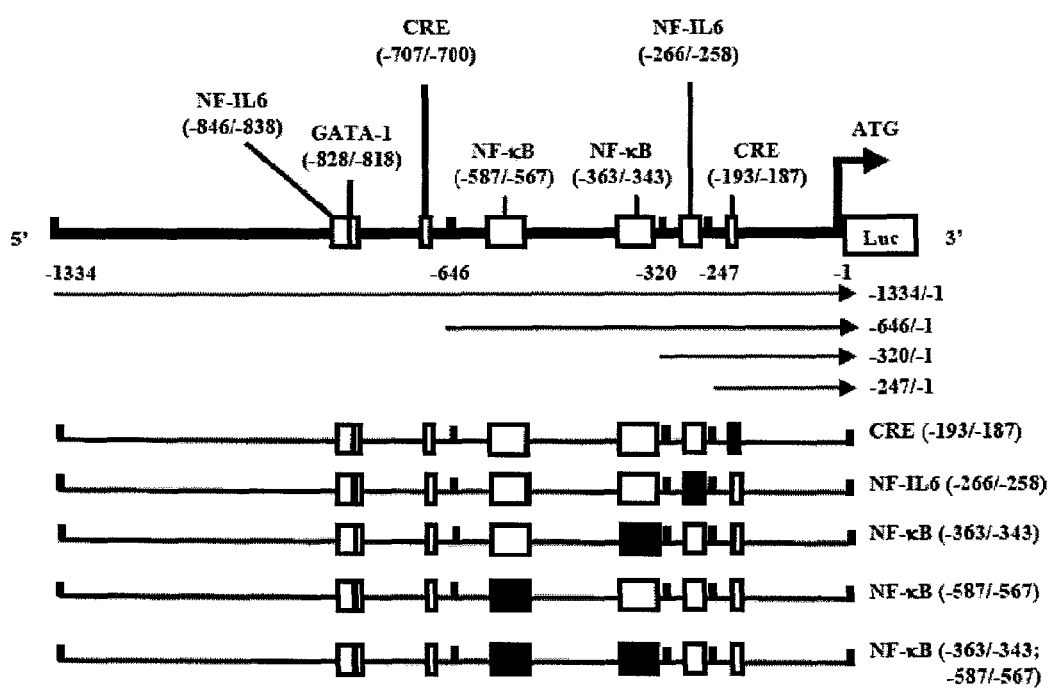
FIG. 2 is a diagram showing luciferase reporter constructs having various promoters.

Four chimeric luciferase reporter genes containing either the full-length 5' flanking promoter region (−1334/−1), or the truncations −646/−1, −320/−1, and −247/−1 bp regions of the human COX-2 promoter were constructed in the pPGL3-Basic vector (Promega) by the method described in Chiang et al. Br J Pharmacol 2005; 146:352-63. Another series of promoter constructs with specific mutations on the consensus sequences CRE, NF-IL6, and NF-κB of full-length COX-2 promoter were also created using PCR-based site-directed mutagenesis (Cheng et al. Biochemistry 2002; 41; 8759-66). Primer pairs for the mutations had the following sense strand sequences: CRE (−93/−187): 5'-GAAACAGTCATT AGCTCACATGGGCTTG-3' (SEQ ID NO: 1); NF-IL6 (−266/−258): 5'-CACCGGGCTT AGTGCATTTTTTTTAAGGG-3' (SEQ ID NO: 2); NF-κB (−363/−343): 5'-CAGGAGAGTG CCCACTACCCCCTCTGCT-3' (SEQ ID NO: 3); and NE-κB (−587/−567): 5'-CGGGAGAG CCCATTCCCTGCGCCCCGG-3' (SEQ ID NO: 4). A double-mutated COX-2 promoter containing mutations on both NE-κB sites was also constructed (FIG. 2). PPGL-3-Basic vector was used as a negative control in luciferase assays. COX-2 reporter activity in arbitrary units (AU) was normalized to that for the Renilla luciferase reporter.

RT-PCR Analysis

For each RT-PCR analysis, 2 μg of total RNA isolated with TRIZOL® Reagent was used to synthesize $1^{st}$-strand cDNA using SUPERSCRIPT™ II Reverse Transcriptase (Invitrogen). The iNOS and COX-2 genes were amplified and analyzed using specific oligonucleotide primers and PCR reactions by method described in Chiang et al. Br J Pharmacol 2005; 146:352-63).

Western Blotting

Total cellular proteins and the specific cytosolic and nuclear proteins were prepared using methods described in Chiang et al. Protein content was measured by the Bradford method (Bio-Rad). Protein was resolved by 5-20% gradient SDS-PAGE and subjected to immunoblotting using enhanced chemiluminescence reagents (ECL, Amersham). Monoclonal antibodies against PARP (Transduction Laboratories, Lexington, Ky.), GA3PDH (Biogenesis, Poole, UK), α-tubulin (Oncogene Science, Cambridge, UK), COX-2 (Cayman Chemical), phospho-(Ser32)-IκBα, phospho-IKKα (Ser180)/IKKβ(Ser181) (New England Biolabs, Beverly, Mass.), iNOS, IκBα, IKKα/β or NF-κB p65 (RelA) (Santa Cruz Biotechnology, Santa Cruz, Calif.) were used.

Immunoprecipitation and IKK Kinase Assay

Whole cell lysates (300 μg) of macrophages were pre-cleaned by incubation with 0.25 μg IgG and 20 μL protein A/G plus agarose beads (Santa Cruz) for 30 minutes at 4° C. Supernatants were then collected and incubated with IKKα/β antibody and protein A/G plus agarose beads at 4° C. overnight. Precipitates were washed with an IP buffer and a kinase buffer. IKK kinase activity was assayed by adding 1 μg of GST-IKBa fusion protein (Santa Cruz) and 200 μM ATP in 20 μL kinase buffer for 30 minutes at 30° C. and then stopped by mixing with the Laemmli's loading buffer and heated at 100° C. for 5 minutes. Samples were then subjected to immunoblotting.

Immunohistochemical Study of COX-2 and Nitrotyrosine Protein Expressions in Mouse Skin Female ICR mice were topically treated on their shaven backs with vehicle (acetone), TPA, or SNP for 4 hours, or were treated with compound (dLGG, celecoxib, or PTIO) topically for 30 minutes before treating with TPA or SNP for 4 hours and finally killed by cervical dislocation. The formalin-fixed, paraffin-embedded skin tissues were stained according to Chiang et al. Br J Pharmacol 2005; 146:352-63.

Electrophoretic Mobility Shift A(EMSA)

EMSA was performed with the LIGHTSHIFY™ Chemiluminescent EMSA kit (Pierce Biotechnology, Rockford, Ill.). Four microgram of nuclear extract was incubated with biotin end-labeled NE-κB oligonucleotide, 5'-ATGTGA GGGGACTTTCCCAGGC-3' (SEQ ID NO: 5) for 20 minutes at room temperature. The DNA-protein complexes were subjected to 5-10% gradient PAGE. Competition assay with unlabeled oligonucleotide (cold DNA) was performed in parallel.

Confocal Microscopy Study

RAW 264.7 cells were seeded in chamber slides for 1 hour, and then treated with DMSO or dLGG (75 μg/mL) for 1 hour, with or without LPS stimulation for an additional 90 minutes. The cells were fixed, permeabilized with 0.1% Triton X-100, and stained with Hoechst 33342 (DNA marker), FITC-labeled anti-α-tubulin Ab (cytoplasm marker), or rabbit anti-p65 antibody visualized with goat anti-rabbit Rhodamine Red-labeled secondary antibody for analysis with a Zeiss LSM 510 META confocal laser-scanning microscope.

In Vivo Inhibition of Tumor Growth

The chemopreventive effect of the CREa8 subfraction was evaluated on tumor growth using the B16 melanoma C57BL/6J mouse system. Six-week-old animals (4 groups of mice, 5 in each group) were used in this experiment. Group 1 mice (Sham control) were intraperitoneally (ip.) injected with 20 μL of DMSO every 2 days throughout the experimental period, except 100 μL PBS was injected on day 0. Group 4 mice (Tumor control) were pre-treated with DMSO every 2 days, starting from day-14, for 2 weeks, inoculated with B16 tumor cells ($1 \times 10^6$ cells/100 μL PBS) subcutaneously (s.c.) on the abdominal area on day 0, and then injected with DMSO every 2 days until day 21. Group 2 mice were ip. pre-treated with CREa8 (10 mg/kg body weight per dose) every 2 days, starting from day-14, for 2 weeks, s.c. inoculated with B16 tumor cells on day 0, and then continuously treated with CREa8 (ip.) every 2 days until day 21. Group 3 mice were similarly pre-treated with DMSO every 2 days for 2 weeks, inoculated with B16 tumor cells on day 0, and then treated with cisplatin (ip.) every 2 days until day 21. The test mice were monitored daily, and body weights and tumor size (average of 2 dimensions) recorded every 2 days. At the end of the experiment (day 21), tumors were excised and weighed.

The mouse CREa8 dose (10 mg/kg body weight) in this study can be converted to an human equivalent dose (HED) on the basis of body surface area using the formula (FDA, USA, www.fda.gov/cber/gdlns/dose.htm): HED=animal dose in mg/kg×(animal weight in kg/human weight in kg)$^{0.33}$, where the exponent 0.33 is used to account for the difference in body surface area between mouse and human: a dose of 10 mg/kg in a 20 g mouse converts to 0.712 mg/kg in a 60 kg human.

Statistical Analysis

Data are expressed as means±SD. Statistical significance of differences between treatments was determined by ANOVA with Fisher's post hoc test. $P<0.05$ was considered to be statistically significant.

Results

Preparation and Test of Extracts

Whole plant materials of *C. rabens* were ground and extracted with use of methanol (MeOH), followed by successive extraction with EA and n-butanol (BuOH) to yield EA, BuOH and water fractions. These 3 fractions from *C. rabens* were subjected to nitric oxide (NO) production and COX-2 promoter activity assays as described below. The active EA fraction was then further fractionated and tested to obtain the bioactive subfraction CREa8.

NO plays an important role in many normal or pathophysiological processes and was synthesized at high levels by iNOS in mitogen-stimulated immune cells. The LPS-induced inflammatory events in murine macrophages were used in this invention as the in vitro assay model for screening enriched and bioactive fractions/phytocompounds from medicinal plants, potentially used as the candidates of chemopreventive agents.

RAW 264.7 macrophage cells were treated with or without various concentrations of CREa8 extract for 1 hour, then LPS (1 μg/ml) was added and incubated for 24 hours. Vehicle controls were obtained from cells treated with 0.5% DMSO only. NO in the culture medium was measured. Percentage of cell viability was also determined using MTT assay. The data represent 3 experiments and are expressed as mean±SD. The statistical analyses between LPS and CREa8 treatment were performed using Student's t-test.

It was found that NO production in LPS-activated RAW 264.7 macrophages was significantly inhibited by treatment with the CREa8 fraction in a dose-dependent manner. The $IC_{50}$ values for inhibiting NO production in CREa8-treated cells was 11.57 μg/ml. CREa8 had no detectable toxic effect on cell viability of test macrophages at a concentration from 5 to 20 μg/ml, as seen on the results of MTT assay.

HPLC-APCI/MS Analysis of Metabolite Profiling of CREa8 and Structural Elucidation of dLGG The chemical profiling of CREa8 was determined using reverse phase HPLC (FIG. 3A) that were used for monitoring the consistency of the batch-to-batch preparations of the bioactive fraction. On-line APCI/MS was employed for the identification of monogalactosyldiacylglycerol (FIG. 3B). The on-line HPLC-APCI/MS enables direct identification of these monogalactosyldiacylglycerols by use of a RP-18 column [Phenomenex Luna 3μ C18 (2), 150 mm×2.0 mm] and 97% MeOH as solvent, at flow rate of 0.1 ml/min. The fatty acid moieties of the galactolipid compounds in CREa8 were identified as 18:3/18:3, 18:2/18:3, 16:0/18:3, 18:1/18:3, and 16:0/18:2. The sn positioning of the 2 fatty acid moieties in the compounds were not addressed.

Metabolite profiling of the bioactive CREa8 fraction was performed using reverse-phase LC-MS analysis. FIG. 3A shows one major peak and 4 minor peaks on the total ion chromatogram of monogalactosyldiacylglycerol. The atmospheric pressure chemical ionization (APCI)/mass spectrometry (MS) of each peak exhibited the $Na^+$ adduct ($[M+Na]^{·+}$) and fragment ions corresponding to diacylglycerol, monoacylglycerol, and fatty acyl moieties (FIG. 3B). The compound composition of monogalactosyldiacylglycerols in the CREa8 were identified as 18:3/18:3, 18:2/18:3 (2), 16:0/18:3 (3), 18:1/18:3 (4), and 16:0/18:2 (5). The major and active constituent compound containing 18:3/18:3 moieties is designated as dLGG which is also used as the index compound of the CREa8 with a range of content between 15-60% in the fraction. The chemical structure of dLGG was then further elucidated according to MS and NMR spectral data.

Effect of CREa8 on Transcriptional Activity of COX-2 Promoter

Murine melanoma B-16 cells co-transfected with the full-length pCOX-2-Luc and internal control plasmid pRL-TK-Luc plasmid constructs were stimulated without (control) or with TPA, in the absence or presence of the indicated concentrations of CREa8. An amount of 10 μg of total protein lysate was subjected to dual luciferase reporter assay. The induction fold of COX promoter activity by TPA treatment only is presented as 100%. The statistical analyses between LPS and CREa8, aspirin, or indomethacin (Indo.) treatment were performed using Student's t-test.

The biological functions of COX-2 provide an important opportunity to explore the possible mechanism for its role in carcinogenesis. Therefore, COX-2 inhibitors have been proposed for their potential role in human cancer chemoprevention. In recent years, scientific and clinical research efforts have continuously contributed to identifying potent COX-2 inhibitors for human cancer prevention. Here, a COX-2 promoter-driven luciferase reporter assay was used as a rapid experimental system to identify bioactive fractions or phtyochemicals from medical plants as potential chemopreventive agents.

Tumor promoter 12-O-tetradecanoylphorbol-13-acetate (TPA) was reported to act as a potent inducer for COX-2 expression in various cell types, such as macrophages and monocytes. To verify whether the anti-inflammatory properties of CREa8 contribute to its anti-tumor promoting activity, we examined the effect of CREa8 on COX-2 gene (COX-2) activity in TPA-treated B16 melanoma cells. TPA significantly induced the transcriptional activity of the full-length COX-2 promoter in B16 cells, as compared with that in the control cells treated with vector only.

It was found that the TPA-induced COX-2 promoter activity in B16 cells was downregulated by CREa8 dose-dependently. The addition of 50 and 100 mg/ml CREa8 to TPA-treated B16 cells resulted in the decrease of full-length cox-2 promoter activities, which are 87% and 73%, respectively, to that of the cells treated with TPA only (100%).

dLGG Significantly Inhibits NO Production In Vitro and In Vivo

The inhibition of LPS-induced NO production by *C. rabens* extracts or purified dLGG was investigated in murine RAW 264.7 macrophages by determination of nitrite level (equivalent to NO level) in culture medium 24 hours after treatment. Cells ($2×10^5$ cells/well) seeded in 96-well plates were treated with or without various concentrations of test compounds in 0.5% DMSO (vehicle control) for 1 hour then LPS (1 μg/mL) was added and incubated for 24 hours. NO in the culture medium was measured using the Griess reagent. Survival of macrophages after treatment was measured using MTT assay and calculated by the following formula: viable cell number (%)=$OD_{570}$ (treated cell culture)/$OD_{570}$ (vehicle control)×100. One-way ANOVA was used to analyze significance of differences.

It was found that dLGG significantly inhibited LPS-induced NO production in RAW 264.7 cells in a dose-dependent manner. The 50% inhibitory concentration of dLGG was approximately 11.4 μg/mL (=14.7 μM). In MTT assays, dLGG (5 to 20 μg/mL) did not have detectable cytotoxicity on test macrophages.

To examine the capability of dLGG to scavenge NO in vivo, the plasma NO concentration in SNP-insulted mice was determined with or without pretreatment with dLGG. Female ICR mice were transdermally treated with 200 μL acetone (vehicle control) or SNP (5.96 mg/site) only for 15 minutes, or pre-treated with dLGG (10 mg/site) or PTIO (3.5 mg/site) for 30 minutes before SNP treatment.

It was found that the nitrite plasma concentration was significantly increased in SNP-treated mice as compared to the vehicle-treated mice. This induced increase was suppressed by pretreatment with dLGG or PTIO, a known NO scavenger, suggesting that dLGG is a potent NO scavenger in vivo.

dLGG Inhibited iNOS mRNA and Protein Expression

The effect of dLGG on iNOS mRNA and protein expression was examined in LPS-stimulated macrophages.

RAW264.7 cells were treated with various concentrations of dLGG for 1 hour, then incubated with LPS (1 μg/mL) for 6 hours. Total cellular RNA was subjected to RT-PCR, and final PCR product resolved by 1% agarose gel electrophoresis. It was found that dLGG significantly down-regulated iNOS mRNA expression, with approximately 56% reduction at 50 mg/mL, suggesting that dLGG modulates iNOS at the transcriptional level.

RAW264.7 cells were treated with the indicated concentrations of dLGG for 1 hour then LPS (1 µg/mL) was added for 18 hours. Total cellular protein (20 µg) was then subjected to immunoblotting. Quantification of iNOS mRNA and protein expression involved normalization to GA3PDH (internal control) by densitometry. The result showed significant inhibition at the protein level after an 18 hours treatment. Little iNOS protein was detected at 25-75 mg/mL dLGG. Thus, the dLGG-induced inhibition of NO production in LPS-stimulated macrophages is also mediated through suppression of both transcription and translation of iNOS.

dLGG Inhibited Enzymatic Activity and Protein Expression of COX-2 and $PGE_2$ Production The above-mentioned test compounds were incubated with COX-2 enzyme and substrates before measuring the COX-2 activity. Celecoxib, a potent nonsteroidal anti-inflammatory drug (NSAID), was used as a positive control. It was found that COX-2 activity in macrophages was significantly inhibited by dLGG, with an $IC_{50}$ of 4.15 µg/mL. The $IC_{50}$ of the nonsteroidal anti-inflammatory drug celecoxib, used as a positive control, was 0.47 µg/mL. RAW 264.7 cells ($1 \times 10^4$ cells/well) were treated with dLGG and then stimulated with LPS, and $PGE_2$ in the culture medium was then measured. It was found that LPS-induced $PGE_2$ levels in macrophages were significantly reduced (37-58%) by dLGG at doses between 25 and 75 µg/mL.

It was further examined whether dLGG affects COX-2 mRNA and protein expression using RT-PCR and immunoblotting. Cells were treated with dLGG for 1 hour, then LPS (1 µg/mL) was added for 18 hours. Total cellular protein (20 µg) was subjected to immunoblotting. Quantification of COX-2 mRNA and protein expression involved normalization to GA3PDH by densitometry. It was found that while dLGG only moderately suppressed COX-2 mRNA expression (~29% inhibition at 75 µg/mL), COX-2 protein levels were significantly decreased in a dose-dependent manner. dLGG (50 µg/mL) suppressed LPS-induced COX-2 protein synthesis by approximately 60%, and at 75 µg/mL, COX-2 protein was barely detectable.

dLGG Inhibited Transcription of COX-2

The effect of dLGG on COX-2 gene activity in TPA-treated B16 melanoma cells was examined. To evaluate whether important cis-acting elements located in the COX-2 promoter region were affected by TPA or dLGG treatment, a series of COX-2 promoter-luciferase reporter genes were constructed (FIG. 2).

B-16 cells were co-transfected with the full-length pCOX-2-Luc and internal control Renilla pRL-TK-Luc plasmid constructs with the LIPOFECTAMINE reagent (Invitrogen). The cells were then stimulated with vehicle (0.001% DMSO) or with 50 ng/mL TPA, in the absence or presence of dLGG for 6 hours. Ten µg of total protein lysate prepared with Passive Lysis Buffer (Promega) was subjected to dual luciferase reporter assay. The induction fold of COX-2 promoter activity by TPA treatment only is presented as 100%.

It was found that TPA-induced COX-2 promoter activity in transfected B16 cells was down-regulated by dLGG in a dose-dependent manner. At 50 or 100 µg/mL, dLGG suppressed full-length COX-2 promoter activities by 20 and 33%, respectively, compared to cells treated with TPA only (100%). Reference controls aspirin (45 µg/mL) and indomethacin (15 µg/mL) suppressed COX-2 promoter activity by 19 and 28%, respectively.

COX-2 promoter activities of −1334/−1, −646/−1, −320/−1, and −247/−1 constructs were also examined in control cells or B16 cells treated with TPA only or TPA+dLGG. The full-length COX-2 promoter was found to be highly sensitive to TPA treatment (1.9-fold increase in luciferase activity) in B16 melanoma cells. Increasing promoter truncation decreased the sensitivity to TPA induction, where the −646/−1 construct showed a 1.45-fold increase in luciferase activity and the −320/−1 construct increased only 1.27-fold. The shortest construct (−247/−1) was not responsive to TPA. In the presence of 100 µg/mL of dLGG, the TPA-induced luciferase activity of cells containing −1334/−1 and −646/−1 promoter constructs (black bars) was significantly smaller (65-68%). There was no difference between TPA-stimulated cells treated with dLGG and the respective background luciferase activity of all transfected cells, showing that dLGG was able to fully inhibit any TPA-activated increases in luciferase activity.

The contribution of specific cis-acting element binding sites on the transcription of COX-2 was examined. Data were obtained from 2 to 3 experiments with 3 to 6 replicates and expressed as mean±SD. Two-way ANOVA was used to analyze significance of differences. TPA effectively induced COX-2 promoter-directed luciferase activity in those constructs containing single or double mutations of the NF-IL6 or NF-κB binding sites, but not the CRE mutant. Importantly, dLGG was able to suppress this TPA-induced COX-2 promoter activity in all mutant promoter constructs, so that luciferase activity was the same as in the respective vehicle controls. These results indicate that the CRE is a critical regulatory motif for TPA-induced COX-2 transcription, while the CRE, NF-IL6, and NF-κB binding sites might play an equally important role in dLGG inhibition of COX-2 promoter activity.

dLGG and CREa8 Suppressed TPA-Induced COX-2 and Nitrotyrosine Protein Production Immunohistochemical study was carried out to examine the ability of dLGG to inhibit TPA induction of COX-2 and nitration of proteins in vivo using immunohistochemical analysis in a mouse skin system. Dorsal skin of female ICR mice was treated topically with acetone (vehicle control) or TPA (10 nmol) for 4 hours or with various concentrations of dLGG or celecoxib for 30 minutes before TPA treatment for 4 hours. Immunohistograms were taken with an Olympus DP-70 camera on a Nikon ECLIPSE E800 microscope. It was found that, after treatment with TPA (10 nmol in 200 µL/site) for 4 hours, levels of COX-2 and of nitrotyrosine-containing proteins increased significantly in the epidermis, and that these increases were significantly attenuated by dLGG in a dose-dependent manner. The inhibitory effect on COX-2 protein expression and on nitrotyrosine-containing proteins from dLGG at 1 mg in 200 µL/site (6.46 mM) was comparable to that of celecoxib at 10 mg in 200 µL/site (130 mM). Similar experiments were carried out using CREa8 and similar results were obtained.

dLGG Prevented NF-κB p65 Nuclear Translocation by Suppressing IκBα Phosphorylation and Degradation Effects of dLGG on IκBα phosphorylation and degradation, and NF-κB translocation in RAW 264.7 cells were examined.

Cells were treated with various concentrations of dLGG for 1 h followed by the addition of LPS (1 µg/mL) for 30 min. Western blots was then conducted using antibodies for IκBα or phospho-IκBα. It was found that the LPS-induced phosphorylation of IκBα in macrophages was inhibited by dLGG as the p-IκBα level decreased when the concentration of dLGG rose. The inhibition of IKBa phosphorylation also prevented IκBα degradation: IκBα continued to be detected in the presence of dLGG.

The distribution of NF-κB (p65) in nucleus and cytoplasm was determined using immunoblotting. Cells were treated with various concentrations of dLGG for 1 hour and then stimulated with LPS (1 µg/mL) for another 90 min. Nuclear and cytosolic fractions were immunoblotted with p65 NF-κB antibody. A slight increase in nuclear p65 protein (1.5-fold) was detected when macrophages were treated with a low concentration of dLGG (5 µg/mL), compared to LPS alone (1.0). With higher concentrations of dLGG (25 to 75 µg/mL), the level of nuclear p65 decreased accordingly. Cytoplasmic levels of NF-κB (p65) were not affected by dLGG treatment of LPS-stimulated macrophages.

The effect of dLGG on NF-κB (p65) nuclear translocation was also examined by confocal microscopy. Macrophages were treated with 0.4% DMSO, or LPS (1 µg/mL) with or without dLGG (75 µg/mL), and stained with fluorescence-labeled antibodies against p65 (red). To distinguish nucleus from cytosol, cells were also stained with DNA-specific Hoechst 33342 (blue) and with anti-α-tubulin antibody (green). In vehicle-treated cells, p65 protein was mainly found in the cytosol of test cells. After stimulation with LPS, p65 translocated from the cytosol to the nucleus, as seen in the overlapping blue and red (purple to pink) images. This p65 nuclear translocation was drastically inhibited by dLGG, as the stained p65 protein (red) remained in the cytoplasm.

dLGG Inhibited LPS-Induced Degradation of IRAK-1 and IKKα/β Phosphorylation and IKK Kinase Activity Assays were carried out in RAW 264.7 cells to examine the effects of dLGG on levels of IKKα/β and phospho-IKKα/β, the upstream kinase of IκBα in the NF-κB signaling pathway, and the upstream kinase, IRAK-1, for activating IKK complex. Cells were pretreated with various concentrations of dLGG for 1 hours, followed by LPS stimulation (1 µg/mL for 30 min). Specific IKKα/β and the phosphorylated forms of IKKα/β or GST-IκBα were detected by immunoblotting. IKKα/β immunoprecipitates were prepared from total cell lysate using anti-IKKα/β antibody and subsequently subjected to IKK kinase assay using GST-IκBα as substrate. PARP (nuclear protein) and α-tubulin (cytosolic protein) were used as loading controls.

It was found that dLGG inhibited the LPS-induced phosphorylation of IKKα/β, whereas IKKα/β levels were little affected. In addition, dLGG inhibited IRAK-1 degradation in LPS-stimulated macrophages.

IKK enzymatic activity was also determined to confirm whether it was correlated to the inhibition of IκBα phosphorylation by dLGG. Immunoprecipitated IKK proteins obtained from control cells (±LPS/−dLGG) or cells treated with LPS+dLGG were assayed for phosphorylation of GST-IκBα. The LPS-induced enzymatic phosphorylation of IκBα (p-IκBα) was decreased approximately 42% when treated with 75 µg/mL dLGG. The levels of immunoprecipitated IKK proteins were not affected by dLGG. This result demonstrates that dLGG abolished IκBα phosphorylation through inhibition of phosphorylation of IKKα/β and IKK kinase.

dLGG Inhibited NF-κB Binding to Consensus DNA Sequence

RAW 264.7 cells were pre-incubated in the presence or absence of dLGG (75 µg/mL) for 1 hour and subsequently stimulated with LPS (1 µg/mL) for 60, 90, 120, and 180 min, respectively. EMSA was conducted to examine inhibitory effects of dLGG on LPS-induced activation of NF-κB. It was found that stimulation of RAW 264.7 cells with LPS triggered a consensus KB DNA element binding by NF-κB.

Cells were treated with indicated concentrations of dLGG for 1 hour followed by treatment with LPS (1 µg/mL) for 90 min. Nuclear extracts (4 µg) were subjected to EMSA with a biotin-labeled DNA probe containing the NF-κB binding site. dLGG time-dependently and dose-dependently inhibited NF-κB-DNA binding activity: NF-κB-DNA complex levels with 75 µg/mL dLGG for 60, 90, 120, and 180 min, were 0.43, 0.30, 0.16, and 0.01 times that of LPS alone (1.0), respectively, and 25 and 50 µg/mL dLGG for 90 minutes decreased NF-κB·DNA complex to 77% and 23%, respectively, of LPS alone.

The specific binding of NF-κB to consensus DNA could be completely prevented by the addition of excess cold DNA.

Structure-activity Relationship Study of dLGG Analog

EMSA was used to examine inhibition of NF-κB·DNA binding by dLGG and its structural analogs dLG, 2LGG, 1LGG, LA, and SA. More specifically, RAW 264.7 cells were treated with 1 µg/mL of LPS and dLGG, dLG, 2LGG, 1LGG, LA, and SA, respectively, for 90 min, before EMSA. All compounds were tested at 100 µM, a concentration that showed strong effects with dLGG DNA. Specificity of the NF-κB band was confirmed by incubation with unlabeled NF-κB oligonucleotide (cold DNA).

The inhibitory potencies were: dLGG>dLG>2LGG>1LGG>LA>SA. dLGG and dLG containing dilinolenoylglycerol moieties almost completely inhibited NF-κB·DNA complex formation. 2LGG, 1LGG, and LA with only one linolenoyl chain were less effective than dLGG and dLG; while there was little or no detectable effect for SA. These results suggest that the linolenoylglycerol moiety is the essential galactolipid feature that hinders the formation of the NF-κB·DNA complex.

Inhibition of B16 Melanoma Growth in C57BL/6J Mice by *C. rabens* Extract

The cancer prevention efficacy of the dLGG-rich fraction (CREa8) was examined in vivo in 4 groups of mice according to the method described above. Cisplatin, a cancer chemotherapeutic, was used as a reference control.

Body weights of the experimental mice in 4 groups all increased gradually as a function of treatment time, but with no significant differences among the four groups. From 3 days after inoculation, B16 tumor growth was detected in control mice (Group 1) which grew exponentially over time. Test mice treated with CREa8 (Group 2) and cisplatin (Group 3) showed a significant delay (days 3-7) and inhibition of tumor growth after B16 inoculation (P<0.05). By day 7, tumors of 0.12 and 0.29 cm average size were seen in CREa8- and cisplatin-treated mice, respectively, when the tumor control mice had 0.73 cm tumors. Moreover, the average tumor sizes at day 17 in Group 2 and Group 3 mice were markedly reduced (P<0.05), at only 76% and 73%, respectively, of the tumor control. For days 18 to 21, all surviving mice in the tumor control group had tumors larger than the critical size of 1.5 cm in diameter, at which point test mice were sacrificed as required by Animal Room regulations. In contrast, at the same experimental stage, 3 to 5 mice in both Groups 2 and 3 had tumors<1.5 cm in diameter. Tumors were excised from all test mice on day 21. CREa8 suppressed B16 melanoma growth in vivo more than cisplatin: the tumor weight to body weight ratio at day 21 was significantly lower in CREa8 group (19.7%) (P<0.05) than in cisplatin (25.2%) and tumor control (31.3%) groups. Although previous studies indicated that oral galactolipids are degraded and might not to be absorbed intact by rats (Ohlsson et al. J Nutri 1998; 128:239-45) and are hydrolyzed by human pancreatic enzymes and duodenal contents (Andersson et al. J Lipid Res 1995; 36:1392-400), suggesting a low bioavailability of the unchanged form of dLGG and its derivatives, this study demonstrates that i.p. administration of dLGG can significantly inhibit melanoma growth without mortality or body weight loss.

The naturally abundant galactolipids are glycoglycerolipids with two fatty acids esterified to the glycerol sn-1 and sn-2 positions and one to four galactose units at the sn-3 position. Both natural and synthetic glycoglycerolipids have specific anti-algal, antiviral, antitumour, anti-inflammatory, and immunosuppressive activities. However, the detailed molecular mechanisms of these bioactivities remained to be addressed.

The above study show that C. rabens plant contains a group of monogalactosyldiacylglycerols, differing in chain length and degree of unsaturation in their fatty acyl groups (e.g., C16:0, C18:1, C18:2, and C18:3), as determined by LC-APCI/MS. These compounds dose-dependently inhibited NO production in LPS-stimulated RAW 264.7 macrophages, and the major bioactive component 1,2-di-O-α-linolenoyl-3-O-β-galactopyranosyl-sn-glycerol (dLGG) possesses most significant cancer chemopreventive function.

NO is an attractive therapeutic target because its overproduction has been associated with septic shock, inflammatory diseases, and diabetes. Peroxynitrite-induced protein modifications include protein oxidation or nitration of specific amino acid residues. Unsaturated fatty acids containing bis-allylic protons was suggested to undergo nitration by NO-derived species via multiple mechanisms, and that nitrated fatty acids are potent anti-inflammatory signaling mediators inhibiting LPS-induced secretion of pro-inflammatory cytokines in macrophages. In this light, dLGG containing two linolenic moieties may thus be a scavenger for over-produced NO. It is shown here that dLGG effectively reduced NO in LPS-stimulated macrophages and in the plasma of SNP (a NO donor)-treated mice, and that dLGG also suppressed topical SNP-induced nitroprotein formation in mouse skin, with similar inhibition to PTIO, a NO scavenger. Additionally, dLGG dose-dependently inhibited iNOS mRNA and protein expression in macrophages. This is the first demonstration that a galactolipid is a potent NO scavenger in vitro and in vivo, and the reduction in NO is also partly mediated by gene and protein down-regulation of iNOS.

COX-2 can foster cancer development by enhancing cellular proliferation, rendering cells resistant to apoptosis and promoting angiogenesis. The increased prostaglandin production in different types of cancers, e.g., colon, breast, lung, is associated with increased COX-2 expression. As shown above, inhibition of $PGE_2$ production by dLGG in macrophages was correlated with the attenuation of COX-2 transcriptional, translational and enzymatic activities. COX-2 is an immediate early response gene; its expression is regulated at cis-acting sites by the binding of transcription factors to the COX-2 promoter via transactivation of a regulatory signal. The above study of COX-2 reveal that while the cAMP-responsive element (CRE) is the most important regulatory factor for TPA induction of COX-2 activity in B16 cells, CRE, NF-IL6 and NF-κB binding motifs all contributed to dLGG suppression of COX-2 promoter activity. TPA-induced overexpression of COX-2 protein and protein nitration were effectively suppressed by dLGG, with an efficacy comparable to celecoxib. These results demonstrate that a galactolipid is a potent COX-2 inhibitor in vitro and in vivo.

The translocation of NF-κB to the nucleus is dependent on the phosphorylation, ubiquitination, and proteolytic degradation of IκB. The nuclear NF-κB can then transactivate a number of immune- or inflammatory-related genes. As shown above, the inhibitory effect of dLGG on NF-κB nuclear translocation was due to the inhibition of LPS-induced degradation of IRAK-1, and prevention of phosphorylation and degradation of IκB through inhibition the phosphorylation of IKKα/β, and IKK kinase activities. The result shows that nuclear NF-κB DNA binding was also significant inhibited by dLGG in LPS-stimulated macrophages. Structure-activity relationship studies revealed that galactolipids containing dilinolenoylglycerol moieties (dLGG and dLG) were the most significant inhibitors of NF-κB DNA binding. In addition, the unsaturated LA (C18:3) was more effective than SA (C18:0). Similar inhibitory activity of dLGG analogs on NO production was also observed. Therefore, the linolenoylglycerol element of dLGG plays a critical role in preventing NF-κB transactivation and NO production in LPS-stimulated macrophages.

IRAK-1 was reported to be one of the very upstream molecules activated by a adaptor protein, MyD88 (myeloid differentiation primary response gene 88), in the MyD88-dependent pathway which leads to the translocation of NF-κB into nucleus and this in turn can regulate the expression of many genes related to proinflammatory mediators. We have also observed that dLGG can dose-dependently suppress the binding of FITC-labeled LPS to the test macrophages. Taken together, our results show that dLGG attenuates the activity of NF-κB and its downstream inflammatory mediators, NO, iNOS, COX-2 and $PGE_2$ in RAW264.7 cells stimulated with LPS, probably due to the suppression of LPS binding to LPS receptors on the cells and the down-regulation of the MyD88 dependent pathway.

Botanical preparations have been used for treatment and prevention of various human diseases throughout history. However, as the active ingredients in plants and their mechanisms of action are usually poorly understood, scientific study of the bioefficacy and pharmacological effects of medicinal plants is urgently-needed. This invention provides new insight into the molecular mechanism(s) underlying the anti-inflammatory bioactivities of a natural galactolipid dLGG from C. rabens.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. An extract prepared from *C. rabens*, wherein the extract is prepared by a process comprising:

mixing a *C. rabens* plant with alcohol to form a first solution;

removing alcohol from the first solution to obtain a second solution;

adding ethyl acetate to the second solution to form an organic portion and an aqueous portion;

separating the organic portion into a multiple fractions; and collecting a fraction containing 1(2)-O-α-linolenoyl-2(1)-O-α-linoleoyl 3-O-β-galactopyranosyl-sn-glycerol (18:3/18:2) (dLLGG).

2. The extract of claim 1, further comprising 1,2-di-O-α-linolenoyl-3-O-β-galactopyranosyl-sn-glycerol (dLGG).

3. The extract of claim 2, wherein the weight ratio of dLGG to dLLGG is 1:0.1 to 1:0.3.

4. The extract of claim 2, further comprising 1(2)-O-α-linolenoyl-2(1)-O-α-palmitoyl 3-O-β-galactopyranosyl-sn-glycerol (18:3/16:0), wherein the weight ratio of dLGG to 1(2)-O-α-linolenoyl-2(1)-O-α-palmitoyl 3-O-β-galactopyranosyl-sn-glycerol (18:3/16:0) is 1:0.001-0.1.

5. The extract of claim 1, wherein the organic portion is separated on a silica gel column with a solution containing dichloromethane and methanol to obtain the fraction containing dLGG.

6. The extract of claim 1, further comprising a monogalactosyldiacylglycerol of formula I:

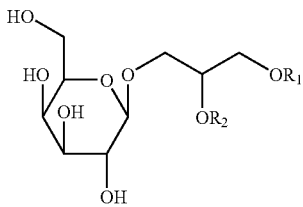

wherein each of $R_1$ and $R_2$, independently, is $C(O)R_a$ in which $R_2$ is $C_{15-17}$ alkyl having 0 to 3 double bonds.

7. The extract of claim 6, wherein the monogalactosyldiacylglycerol is selected from the group consisting of 1,2-di-O-α-linolenoyl-3-O-β-galactopyranosyl-sn-glycerol (dLGG), 1(2)-O-α-linolenoyl-2(1)-O-α-palmitoyl 3-O-β-galactopyranosyl-sn-glycerol (18:3/16:0), 1(2)-O-α-linolenoyl-2(1)-O-α-oleoyl 3-O-β-galactopyranosyl-sn-glycerol (18:3/18:1), and 1(2)-O-α-linoleoyl-2(1)-O-α-palmitoyl 3-O-β-galactopyranosyl-sn-glycerol (18:2/16:0).

8. The extract of claim 1, wherein the extract inhibits NO production of a cell.

9. The extract of claim 1, wherein the extract inhibits the expression of iNOS or COX-2 in a cell.

10. The extract of claim 1, wherein the extract inhibits the activity of NF-κB in a cell.

11. A composition consisting essentially of the extract of claim 1, a carrier, and optionally 1,2-di-O-α-linolenoyl-sn-glycerol (dLG), 2-O-α-linolenoyl-3-O-β-galactopyranosyl-sn-glycerol (2LGG), or 1-O-α-linolenoyl-3-O-β-galactopyranosyl-sn-glycerol (1LGG), or a combination thereof.

12. The composition of claim 11, wherein the carrier is a cosmetically acceptable carrier.

13. The composition of claim 11, wherein the carrier is a pharmaceutically acceptable carrier.

14. The composition of claim 11, consisting essentially of the extract of claim 1, a carrier, and 1,2-di-O-α-linolenoyl-sn-glycerol (dLG), 2-O-α-linolenoyl-3-O-β-galactopyranosyl-sn-glycerol (2LGG), or 1-O-α-linolenoyl-3-O-β-galactopyranosyl-sn-glycerol (1LGG), or a combination thereof.

* * * * *

SEQUENCE LISTING

<160> NUMBER OF SEQ ID NOS: 5

<210> SEQ ID NO 1
<211> LENGTH: 28
<212> TYPE: DNA
<213> ORGANISM: Artificial Sequence -continued

```
<220> FEATURE:
<223> OTHER INFORMATION: Description of Artificial Sequence: Synthetic
      primer

<400> SEQUENCE: 1
gaaacagtca ttagctcaca tgggcttg                                          28

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
caccgggctt agtgcatttt tttaaggg                                          28

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
caggagagtg cccactaccc cctctgct                                          28

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cgggagagcc cattccctgc gccccgg                                           28

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
atgtgagggg actttcccag gc                                                22
```